United States Patent [19]

Andary et al.

[11] 3,954,407
[45] May 4, 1976

[54] AUTOMATIC TOOTHBRUSH STERILIZER

[76] Inventors: William A. Andary, 300 Armory Place; Corydon L. Somes, 1309 John St., both of Sault Ste. Marie, Mich. 49783

[22] Filed: Sept. 12, 1974

[21] Appl. No.: 505,314

[52] U.S. Cl. ............................... 21/83; 21/102 R; 312/206; 312/223
[51] Int. Cl.² ......................................... A61L 3/00
[58] Field of Search ................. 21/83, 102 R, 54 R, 21/DIG. 2; 312/206, 125, 97.1, 223, 305

[56] References Cited
UNITED STATES PATENTS

| | | | |
|---|---|---|---|
| 2,129,150 | 9/1938 | Pekrol | 21/83 |
| 2,579,242 | 12/1951 | Pask | 312/206 X |
| 2,587,131 | 2/1952 | Ficken | 21/83 X |
| 2,592,131 | 4/1952 | Farrar | 312/206 X |
| 3,309,159 | 3/1967 | Le Seur et al. | 312/206 |
| 3,748,094 | 7/1973 | Scheidell | 21/83 |
| 3,776,694 | 12/1973 | Leittl | 21/83 X |

Primary Examiner—Morris O. Wolk
Assistant Examiner—Arnold Turk
Attorney, Agent, or Firm—Irving M. Weiner; Pamela S. Burt

[57] ABSTRACT

A device for automatically sterilizing toothbrushes when the toothbrushes are not in use. A germicidal lamp and toothbrushes are held within an apertured casing which is mounted on a vertical wall. A dial selector allows one of a plurality of toothbrushes to be aligned with the aperture for removal and replacement of toothbrushes from the casing. Electrical circuitry is provided to act as a switch for the lamp. The lamp is energized only when the aperture is blocked to thereby prevent the potentially dangerous "short" ultraviolet rays emitted by the lamp to escape from the casing.

4 Claims, 4 Drawing Figures

U.S. Patent   May 4, 1976   3,954,407
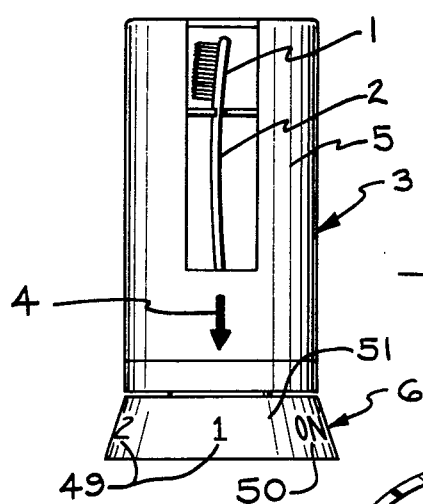
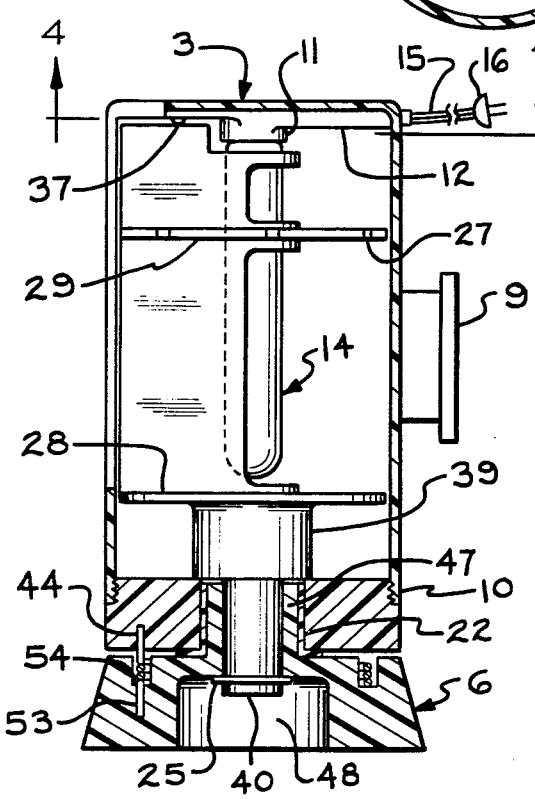
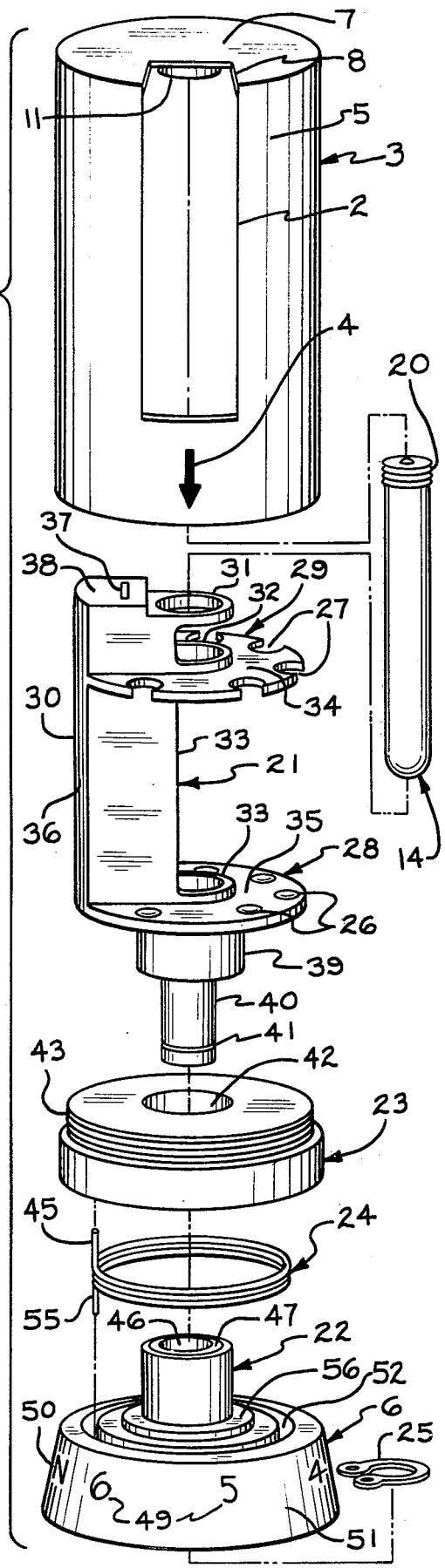

AUTOMATIC TOOTHBRUSH STERILIZER

BACKGROUND OF THE INVENTION

The invention relates generally to a device for sterilizing toothbrushes and more particularly to a device which employs a germicidal lamp to irradiate the air about toothbrushes which are held within a mounted casing for selective removal and replacement therefrom.

Germicidal lamps, the sterilizing element in the present invention, emit short wave ultraviolet radiation. The wavelengths of ultraviolet radiation which are most lethal to disease causing micro-organisms are the short waves in the region of 2537 A. Some germicidal lamps also emit a shorter wavelength of ultraviolet radiation, namely 1849 A. The wavelengths in this particular region have the capacity of creating ozone in the air. Ozone, itself, also being a germicidal agent. Ozone, being a gas, diffuses and sanitizes the places not reached by the ultraviolet rays.

All types of micro-organisms known to man, including bacteria, virus, and mold spores can be destroyed by germicidal ultraviolet rays which directly strike the micro-organisms in the air or on exposed surfaces. The exposure time of the ultraviolet radiation necessary to kill the micro-organisms varies inversely with the intensity of the rays. For example, the average bacterium will be killed in ten seconds at a distance of six inches from a lamp well known in the art.

If one is exposed to direct or reflected high intensity short wave ultraviolet radiation over a prolonged length of time, a painful irritation of the eyes (conjunctivitis) and reddening, or even burns of the skin may result. Any application of germicidal lamps must, therefore, keep this very important fact in mind.

SUMMARY OF THE INVENTION

The present invention relates to the use of a germicidal lamp disposed within a housing which encompasses toothbrushes held on a frame so as to permit the removal and replacement of the desired toothbrush through an aperture in the casing. Electrical circuitry is provided to act as a switch for the lamp in order to de-energize the lamp whenever a toothbrush is about to be removed or replaced.

One object of the present invention is to provide an apparatus for sterilizing toothbrushes by irradiating the air about said toothbrushes with a germicidal lamp disposed within a protective outer casing along with said toothbrushes.

Another object of the present invention is to provide an elongated slot and electrical circuitry within said casing to provide for the easy and safe removal and replacement of toothbrushes from the apparatus which is mounted to a verticle surface.

Another object of the invention is to provide a holding mechanism for toothbrushes which automatically returns to a predetermined position to allow a germicidal lamp to irradiate the air about and the surface of toothbrushes.

BRIEF DESCRIPTION OF THE DRAWINGS

FIG. 1 shows a toothbrush which is about to be removed or has just been placed within the casing through an aperture. The indicator shown on the outer casing is aligned with the numeral "1" located on the base of the apparatus and indicates the fact that the visible toothbrush occupies the number one position on the holding means.

FIG. 2 shows a side view of the disassembled apparatus to show some of the individual elements of the invention and how said elements are positioned relative to one another.

FIG. 3 shows a partial sectional view of the assembled apparatus, particular emphasis being placed on the interrelationship between the intermediate base and the base.

FIG. 4 is a top sectional view of the apparatus along the line 4—4 in FIG. 3, the figure especially shows wire channels for the electrical circuitry required by the invention.

DETAILED DESCRIPTION OF THE PREFERRED EMBODIMENT

FIG. 1 shows a toothbrush 1 through an aperture 2 in a housing means, such as cylindrical casing 3. An indicator means, such as arrow 4, is formed on the outer surface 5 of said casing and directly beneath said aperture. When said arrow is aligned with a numeral formed on the outer surface of base 6, a toothbrush position is aligned in aperture 2. As is shown in FIG. 1, the toothbrush which has been placed in position number 1 is directly aligned with aperture 2.

FIG. 2 shows aperture 2 as an elongated slot formed along the longitudinal axis of said casing and which extends to the top surface 7 of said casing to form an opening 8 therein. Aperture 2 and opening 8 are formed so as to allow easy removal and replacement of toothbrushes.

As is shown in FIG. 3 a mounting bracket 9 is rigidly affixed to the curved outside surface 5 of said casing and substantially opposite said aperture. The entire assembly may thereby be attached to a flat surface such as a bathroom wall.

As can be best seen in FIG. 3, the inner surface of said casing is threaded along its base 10 to accept the holding means which will be described later.

As can be seen in FIGS. 3 and 4 chamber 11 is formed in the approximate center of the inside upper surface 12 of said casing. The inner side wall surface of said chamber is threaded. Said threads consist of an electrically conductive metal, such as copper. A depression 13 is formed in the inner top surface of said chamber. The inner surface of the depression being coated with an electrically conductive metal. Said depression and chamber threads 18 are electrically insulated from one another. Thereby, said chamber acts as an electrical socket for a conventional screw-in germicidal lamp 14.

As can best be seen in FIG. 4 a double strand wire cord 15 extends through the side wall of casing 3 and forms an integral part of the housing means. At one end of said cord a conventional wall plug 16 is operably attached so as to provide a means for supplying electrical power to said invention. At the second end of said cord a first strand makes electrical contact with a first metal contact 17 located on upper surface 12 of said casing between opening 8 and chamber 11. The second strand makes electrical contact with the inner surface of depression 13. The chamber threads 18 make electrical contact with a second metal contact 19 also located on the inside upper surface 12 and immediately adjacent said first metal contact, (note, no electrical contacts are shown in the drawings. This may be done by any method known in the art.)

FIG. 2 shows a conventional germicidal lamp 14 while FIG. 3 shows said lamp in its operable position screwedly inserted in chamber 11. The length of lamp 14 is substantially the same as the length of the toothbrushes that said lamp irradiates.

Lamp 14 is of convention design to produce ultraviolet rays at wavelengths which only only kill microorganisms but also product the germicidal agent ozone. As seen in FIG. 2, the lamp is threaded at its base 20 in a conventional fashion so said lamp may be screwed into chamber 11 and thereby make electrical contact with said chamber threads and said depression.

FIG. 2 shows a holding means for toothbrushes which comprises: a rigid member 21, a bearing means such as bushing 22, an intermediate base 23, a spring loading means such as torsional spring 24, base 6, and a connecting means, such as snap ring 25.

Said rigid member 21 holds toothbrushes in an upright position as shown in FIG. 1. The holding function is accomplished by means of aligned recessions 26 and arcuate openings 27 formed in a first wheel 28 and a second wheel 29, respectively. A circular bore (not shown) is formed in the approximate center of said second wheel to allow said lamp to slide therethrough.

Rigid arm 30 holds the two said wheels apart with corresponding openings 27 and recessions 26 aligned with one another, the two said wheels being integrally formed in a direction substantially transverse the longitudinal axis of said rigid member.

Rigid arm 30 contains three apertured portions 31,32, and 33. Said portions are integrally formed with said arm and extend outwardly in the same direction as said wheels. The colinear apertures in said portions cooperate with concave channel 33 formed on the side wall surface of arm 30 and said circular bore to hold said lamp in a substantially verticle position. Second portion 32 and third portion 33 are integrally formed on the top surfaces 34,35 of wheels 29 and 28, respectively.

A convex outer surface 36 is formed on said arm opposite said concave channel to allow rigid member 21 to rotate within casing 3. Surface 36 also blocks aperture 2 in said casing and thereby prevents the escape of light from germicidal lamp 14 when said lamp is energized.

An electrical contact strip 37 is fixedly attached to top surface 38 of said arm to bridge the gap between first and second metal contacts 17, 19. Said strip making electrical contact at both contacts when arm 30 aligns surface 36 within aperture 2. Said bridging action places germicidal lamp 19 in series with an alternating current power source when plug 16 is inserted in a conventional electrical wall socket.

Rigid member 21 includes a cylindrical member 39 which is coaxially and integrally formed on the bottom surface of wheel 28. Said rigid member also includes a rod 40, coaxially and integrally formed on the bottom surface of said cylindrical member. A snap ring groove 41 is circumferentially formed in the side wall of said rod to accept a connecting means, such as snap ring 25.

Rod 41 extends through hole 42 centrally formed in cylindrical intermediate base 23. Cylindrical member 39 prevents upward motion of said intermediate base along the longitudinal axis of said rod.

The upper side wall surface 43 of intermediate base 23 is threaded so that said intermediate base may be screwingly attached to casing base 10. As can best be seen in FIG. 3 a bore 44 is formed in the bottom surface of said intermediate base to accept the first end 45 on torsion spring 24.

A cylindrical bore 46 is provided through the approximate center of frusto-conical base 6 and stem 47, said stem being integrally and coaxially formed on the top surface of base 6. Bore 46 accepts rod 40 and thereby said rod and base 6 are coupled together within a cylindrical cavity 48 formed in the lower surface of base 6. Said coupling is accomplished by the action of snap ring 25 positioned in said snap ring groove against said base. Thereby rotational movement of base 6 is directly translated to rigid member 21.

A plurality of numbers 49, indicating the toothbrush position in the holding means, and the word "on" 50 are circumferentially placed flush on the outer side wall surface 51 of base 6. Said numbers and word cooperate with arrow 4 to indicate a toothbrush position appearing in aperture 2 and whether said lamp is energized or not.

A spring groove 52 is circumferentially formed in the top surface of base 6 to accept torsion spring 24. A second bore 53 is formed in the bottom surface 54 of said groove to accept the second end 55 of torsion spring 24. The width of said groove is sufficient to compensate for the increase and decrease of torsion spring diameter caused by the rotational displacement of base 6 with respect to intermediate base 23 when said ends of torison spring 24 are in their respective bores.

A bearing means, such as bushing 22 is removable and rotatably positioned on stem 47. Said intermediate base is place about said bushing by way of hole 42 and rests on collar 56 of bushing 22. Said bushing with collar 56 is provided to prevent frictional wear between intermediate base 23 and base 6 after casing 3 is threadedly attached to said intermediate base.

The instant invention is assembled and operates in the following manner. Casing 3 is attached to a bathroom wall through bracket 9. Germicidal lamp 14 is screwed into chamber 11 thereby forming electrical contact with said chamber at said lamp's two terminals formed in lamp base 20.

The holding means is assembled in the following manner: bushing 22 is placed over stem 47 of base 6; torsion spring 24 is placed within groove 52 so that said spring's second end 55 is within bore 53 provided within base 6; intermediate base 23 is thereafter placed over said bushing so as to rest on collar 56 and to allow the first end 45 of said spring to enter bore 44 as formed in intermediate base 23; rod 40 is then slid through hole 42 and bore 46 so snap ring 25 may be placed in snap ring groove 41 provided on said rod, thereby securely fixing base 6 with rigid member 21 to allow the rotational movement of said base to be directly translated to said rigid member.

Casing 3 and the holding means are then threadedly attached at intermediate base 23 and casing base 10. After said attachment, indicator arrow 4 is aligned with the word "on" 50 on base 6, and outer surface 36 of arm 30 blocks aperture 2. In this position contact strip 37 bridges metal contacts 17 and 19 so as to switch said germicidal lamp into a series circuit to be energized when wall plug 16 is inserted in a conventional electrical outlet.

Toothbrushes may now be placed on the holding means by rotation base 6 so the desired position on said holding means, as indicated by arrow 4, appears through aperture 2. This movement of base 6 creates tension in torsion spring 24 which is held in groove 52 and between base 6 and intermediate base 23. Said tension forces one to exert a balancing force to maintain the desired toothbrush position in said aperture. When said position is no longer desired base 6 is either rotated to another toothbrush position and held there, or the base is released. Upon said release the holding means will return to its original position as a result of the tension exerted by said spring.

The movement of the holding means to a toothbrush position also breaks the bridging electrical contact which existed between said strip and the two electrical contacts 17 and 19. Thereby, said germicidal lamp is no longer activated. After release of said base, as aforementioned, outer surface 36 of arm 30 blocks aperture 2 and electrical contact is again established between metal strip 37 and said electrical contacts to energize said lamp.

We claim:

1. An apparatus for sterilizing and storing toothbrushes and the like, comprising, in combination:
   holding means for a plurality of toothbrushes each of which toothbrush has a longitudinal axis;
   said holding means having a longitudinal axis disposed substantially parallel to the longitudinal axes of said toothbrushes held in said holding means;
   a germicidal lamp for irradiating the air about said toothbrushes;
   housing means which cooperate with said holding means to supply electrical power to said lamp whenever the holding means is in a first position with respect to said housing means, and to prevent the supply of electrical power to said lamp whenever said holding means is no longer in said first position;
   said lamp and said holding means being disposed within said housing means;
   said housing means having an aperture therein to permit the removal and replacement of a toothbrush from said holding means when said holding means is no longer in said first position; said holding means blocking the aperture in the housing means whenever the holding means is in said first position; and
   said holding means includes:
   a rigid member, maintaining the longitudinal axes of said plurality of toothbrushes in a substantially parallel relationship to the longitudinal axis of said holding means,
   a base to receive said rigid member, with rotational movement of the base being directly translatable to rotate said rigid member
   an intermediate base rotatably positioned between said base and said rigid member, said intermediate base threadedly accepting said housing means,
   a bearing means positioned between said base and said intermediate base, and
   spring means positioned between said base and said intermediate base so as to produce a torque between said base and said intermediate base when said base is rotated with respect to said intermediate base in a manner to result in movement of the holding means from the first position.

2. An apparatus for sterilizing and storing toothbrushes and the like, comprising, in combination:
   a cylindrical hollow housing;
   brush holding means disposed for rotation within said housing;
   a germicidal lamp mechanically and operably mounted within said housing for irradiating said brushes and the air about said brushes;
   said housing having an aperture therein permitting the introduction and withdrawal of the brush into and from said brush holding means;
   said brush holding means including a rigid arm having a convex outer surface which is larger than said aperture in said housing and which may be rotated with said brush holding means to block said aperture;
   electrical means for supplying electricity to said germicidal lamp;
   said electrical means including a first portion thereof mounted on said housing and a second portion thereof mounted on said brush holding means; and
   means for rotating said brush holding means to selectively align a brush held on said holding means with said housing aperture in which aligned position said first and second portions of said electrical means are out of electrical contact with each other so that electricity is prevented from being supplied to said germicidal lamp, and for rotating said brush holding means to block said housing aperture with said convex outer surface of said rigid arm in which blocked position said first and second portions of said electrical means are in electrical contact with each other so that electricity may be supplied to said germicidal lamp.

3. An apparatus according to claim 2, wherein:
   a bracket is fixedly mounted on said cylindrical hollow housing to facilitate mounting of said housing to a flat external surface.

4. An apparatus according to claim 2, wherein:
   said brush holding means holds a plurality of said toothbrushes each of which toothbrushes has a longitudinal axis;
   said aperture in said housing has a longitudinal axis; and said means for rotating said holding means includes:
   a first base to receive said rigid arm with rotational movement of said base being directly translatable to rotate said rigid arm,
   an intermediate base rotatably positioned between said first base and said rigid arm;
   said intermediate base threadedly receiving said housing;
   bearing means positioned between said first base and said intermediate base; and
   spring means positioned between said first base and said intermediate base to produce a torque between said first base and said intermediate base when said first base is rotated with respect to said intermediate base in a manner to result in movement of the holding means from the first position.

* * * * *